United States Patent
Pratt

(10) Patent No.: US 6,431,272 B1
(45) Date of Patent: Aug. 13, 2002

(54) CONTROLLED SLOW DESCENT BAILER

(76) Inventor: David W. Pratt, 13512 Feather Sound Cir. West, #1401, Clearwater, FL (US) 33760

(*) Notice: Subject to any disclaimer, the term of this patent is extended or adjusted under 35 U.S.C. 154(b) by 0 days.

(21) Appl. No.: 09/776,468

(22) Filed: Feb. 2, 2001

(51) Int. Cl.[7] .............................. E21B 31/08; G01N 1/12
(52) U.S. Cl. ...................... 166/162; 166/99; 73/864.63
(58) Field of Search .................... 166/66, 66.6, 66.7, 166/99, 162, 165; 73/864.02, 864.31, 864.63

(56) References Cited

U.S. PATENT DOCUMENTS

| | | | |
|---|---|---|---|
| 2,951,538 A | * 9/1960 | Martin | 166/162 |
| 4,254,830 A | * 3/1981 | Garney et al. | 166/162 |
| 4,590,810 A | * 5/1986 | Hunkin et al. | 73/864.63 |
| 5,341,692 A | * 8/1994 | Sher et al. | 73/864.63 |
| 5,454,275 A | * 10/1995 | Kabis | 73/864.51 |
| 5,597,966 A | * 1/1997 | Timmons | 73/864.63 |
| 5,878,813 A | * 3/1999 | Ridgeway, Jr. | 166/162 |

FOREIGN PATENT DOCUMENTS

CA 716378 * 8/1965 ................. 166/162

* cited by examiner

Primary Examiner—Frank Tsay
(74) Attorney, Agent, or Firm—Ronald E. Smith; Smith & Hopen, P.A.

(57) ABSTRACT

A bailer having a slow rate of descent into a liquid body to minimize agitation. In a first embodiment, a plug closes the upper end of the bailer and a perforation is formed in the plug. Air in the hollow interior of the tubular main body of the bailer is constrained to flow through the perforation as the bailer fills. A back pressure created by the air prevents rapid descent of the bailer and thus prevents rapid filling of the bailer. When the bailer is being emptied, the perforation prevents a vacuum from forming in the space below the plug and above the liquid level, but it provides a partial vacuum and therefore slows down the rate of flow of the liquid as it exits the bailer. Covering the perforation with a thumb creates a vacuum above the liquid level and stops the flow of liquid from the bailer. This eliminates the need for a tool that unseats the valve of the bailer from its valve seat. In another embodiment, the perforation is eliminated and rings are secured to the tubular main body of the bailer to slow its rate of descent. Additional embodiments include a baffle wall for slowing bailer descent and a stabilizer tube at the lowermost end of the bailer for maintaining the bailer in an upright configuration during its descent.

14 Claims, 5 Drawing Sheets

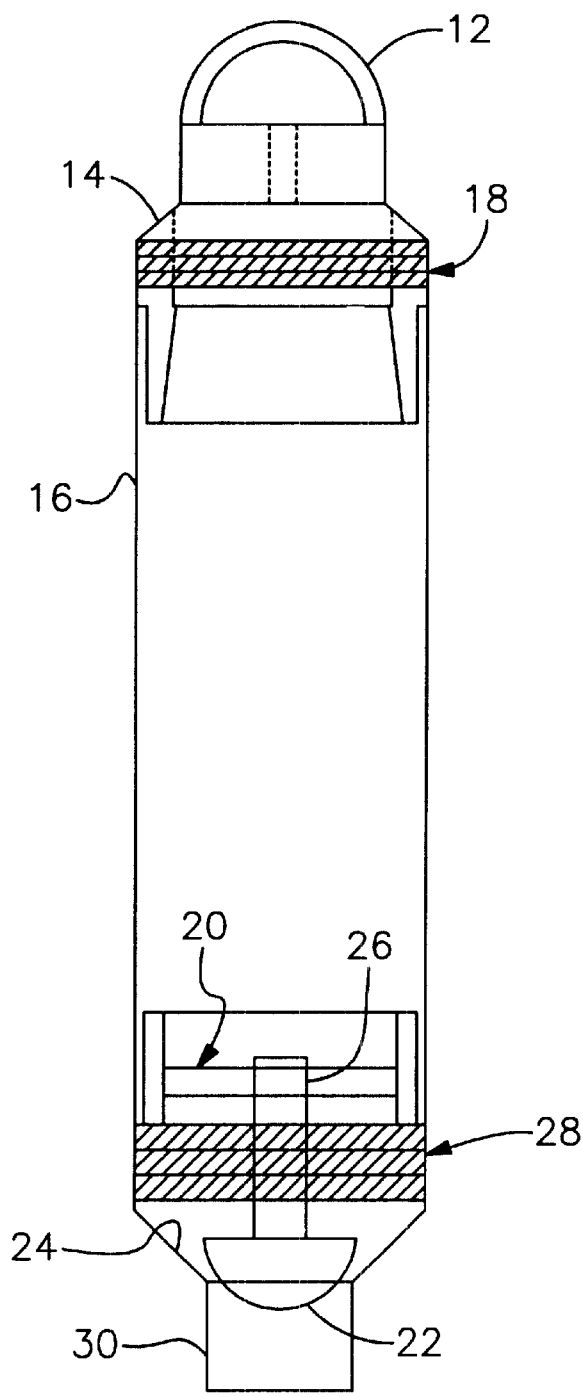
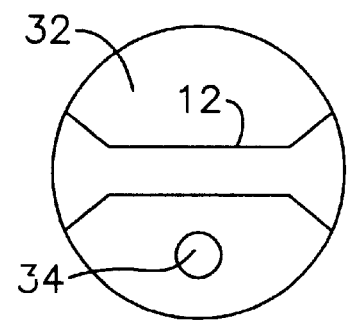
Fig. 2A
Fig. 2

CONTROLLED SLOW DESCENT BAILER

BACKGROUND OF THE INVENTION

1. Field of the Invention

This invention relates, generally, to bailers. More particularly, it relates to a bailer having a construction that controls and slows the rate of descent of the bailer into a liquid fluid to a speed sufficiently slow to substantially avoid agitation of the liquid fluid from which a sample is being taken.

2. Description of the Prior Art

One of the problems confronting the bailer industry is the speed with which samples are normally taken. The people in the field who take samples from wells or other bodies of liquid are generally interested in taking as many samples per day as possible. Accordingly, many developments in the industry have been designed to increase the speed of bailer insertion into a well. For example, there are a number of bailer designs that add weights to a bailer to increase its insertion speed. Unfortunately, this also increases the agitation of the liquid.

Moreover, various environmental protection agencies at the state level are reporting an unacceptably high rate of bad sample data attributed largely to the speed of sample collection. Apparently, a fast-traveling bailer increases agitation and causes turbidity by stirring up sediment and the like that would remain undisturbed if the bailer were entering into and traveling through the liquid fluid at a slower rate. Thus, pollutants are collected that would not have been collected if the bailer had descended and filled at a slower rate. Agitation can also increase the oxygen content of the liquid, thereby generating false data.

There are two relatively obvious solutions to the problem. The first solution, not favored by state agencies, is to provide better training to those who work with bailers in the field so that they will collect the samples at a slower rate. The time and expense that would be required to educate such workers is thought to be prohibitive. Nor do such agencies trust the efficacy of such training.

The second solution, favored by some experts in the field and some governmental authorities, is to ban the use of bailers and to mandate that pumps be employed to collect samples. There are several problems with that solution. Most importantly, perhaps, is the fact that pumps have moving parts capable of stirring up sediment and their use will therefore not solve the agitation and turbidity problems. Moreover, pumps are much more expensive than bailers. A disposable bailer may cost no more than a few dollars but a pumping system can cost from fifteen hundred dollars to triple that amount. It follows that pumps of such expense cannot be used one time and discarded as are bailers. Instead, to avoid cross-contamination between various wells, a pumping system must be thoroughly cleaned after each use. This consumes large quantities of pure water and time.

It has also been proposed that to avoid the cross contamination problem and the time and expense of cleaning a pump after each use, a pump could be permanently installed at each sample collection site, such as a well. This solution is impractical in view of the extremely large number of collection sites. For example, there may be a hundred wells just in one small area near a known source of contamination.

Moreover, pumps require electrical power which is often unavailable in remote collection sites. A portable generator would have to be brought to such locations, thereby driving up the cost of sample collection even higher.

Pumps, then, are clearly not the answer to the problem.

In view of the prior art, considered as a whole, at the time the present invention was made, it was not obvious to those of ordinary skill in the pertinent arts how the problems associated with poor samples based upon excessive bailer speed insertion could be resolved.

SUMMARY OF THE INVENTION

The longstanding but heretofore unfulfilled need for a bailer that descends slowly into a body of liquid and which fills slowly to reduce agitation is now met by a new, useful, and nonobvious invention. The novel bailer includes an elongate, tubular main body having a hollow interior and having an open upper end. A plug closes said upper end and a small perforation of predetermined size is formed in the plug. A check ball and a check ball seat are disposed at a lower end of the bailer and the check ball lifts from the check ball seat when the bailer is lowered into a body of liquid fluid, in response to an inflow of liquid fluid into the elongate, tubular main body. In this way, air positioned below the plug and above the liquid fluid is constrained to flow out of the elongate, tubular main body through the perforation as liquid fluid flows into the elongate, tubular main body. Accordingly, a back pressure is created by the air because the air cannot flow through the perforation at a rate of flow that exceeds the rate of flow of the liquid fluid into the elongate, tubular main body. Thus, the bailer descends slowly into the liquid fluid and the liquid fluid flows slowly into the elongate, tubular main body and agitation of the liquid fluid is reduced.

When the bailer is being emptied, the presence of the plug and the small perforation creates a near vacuum in the space below the plug and above the liquid level because ambient air cannot flow through the perforation into the space as quickly as the liquid fluid can flow from the bailer. This near vacuum thus provides a braking action that prevents rapid outflow of the liquid sample, again reducing agitation.

In a first embodiment, the perforation is formed in the plug and in a boss means that projects upwardly therefrom. The perforation is perhaps more accurately described as a throughbore in that it extends through the boss means and the plug. In a second embodiment, the boss means is eliminated and the throughbore is formed in the plug only.

In a third embodiment, one or more flat baffle walls are mounted to the external wall of the elongate, tubular main body to slow the rate of descent of the bailer. The plug and the perforation formed therein may be eliminated so that the elongate, main tubular body is open at its uppermost end or the plug and perforation formed therein may be maintained and used in conjunction with the baffle wall.

In a fourth embodiment, the baffle wall defines a downwardly opening cavity.

A fifth embodiment includes a stabilizer means in the form of a hollow tube that is secured to the lowermost end of the bailer in leading relation thereto.

A primary object of the invention is to provide a bailer that descends slowly into a body of liquid fluid to reduce agitation and turbidity.

A closely related object is to provide such a bailer that does not require training or educating workers in the field as to their proper use.

Another object is to provide a bailer which may also be emptied slowly.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 2 is a side elevational view of a second embodiment of the novel bailer;

FIG. 2A is top plan view of said second embodiment;

DETAILED DESCRIPTION OF THE PREFERRED EMBODIMENT

Figure 1:
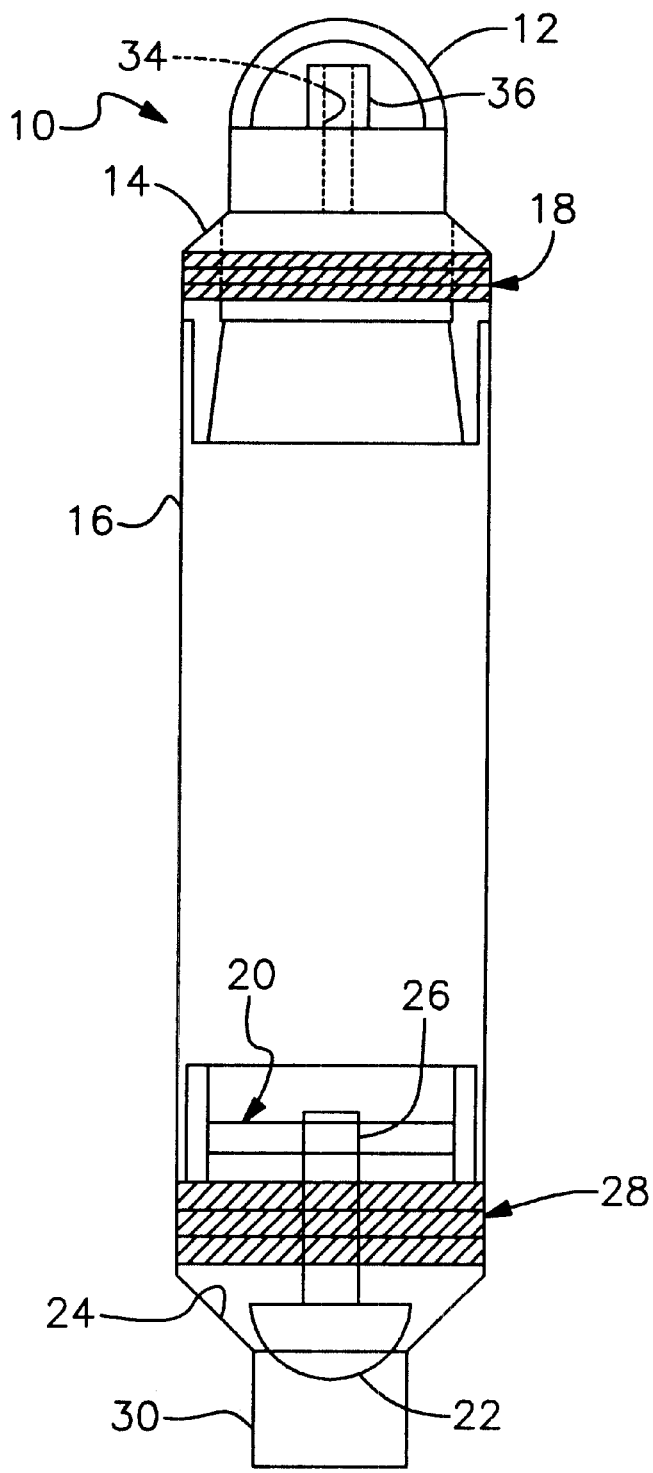
FIG. 1 is a side elevational view of a first embodiment of the novel bailer.
Figure 1A:
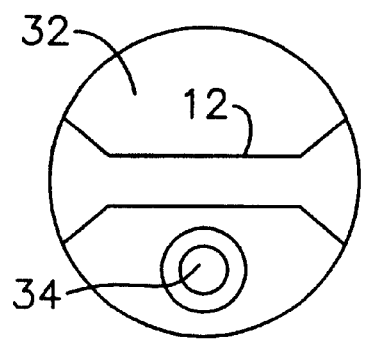
FIG. 1A is a top plan view thereof.

Referring to FIGS. 1 and 1A, it will there be seen that the reference numeral 10 denotes an illustrative embodiment of the present invention. It should be understood from the outset that the invention to be disclosed has utility with bailers of all types and sizes. The bailer denoted 10 is merely one type of bailer and the invention is not restricted to bailers of the type depicted. Bailer 10 includes a handle 12 at its uppermost end to which is secured a rope, not depicted, or other suitable connection means to enable the lowering and lifting of a bailer into and from a liquid body. A weight housing 14 is slidingly received within tubular main body 16 of the bailer and provides a means for holding top weight members, collectively denoted 18. A spider assembly 20 is positioned near the lower end of tubular main body 16 and serves to guide hemispherical valve body 22, known in the industry as a check ball, as it rises and falls with respect to valve seat 24. Valve stem 26 is slidingly received within an aperture formed in the center of spider assembly 20 so that check ball 22 rises and separates from check ball seat 24 when liquid fluid flows into the hollow interior of tubular main body 16 and so that said check ball returns to its seated position against said check ball seat 24 when said liquid fluid has ceased flowing into said tubular main body. A lower set of weights, collectively denoted 28, is provided near the lowermost end of bailer 10. A tubular fluid entry/discharge downspout 30 depends from check ball seat 24.

As perhaps best, understood in connection with FIG. 1A, the uppermost end of weight housing 14 (or the uppermost end of tubular main body 16 if said weight housing is not provided), is closed with a plug 32 having a vent opening or perforation 34 formed therethrough. In this particular embodiment, vent opening 34 is formed in a boss 36 that is formed integrally wilt plug 32. In an illustrative embodiment of the invention, perforation 34 is formed by a needle or pin of common size and has a diameter of about 0.060 inch. The range of diameters is from about 0.030 inch to about 0.10 inch. This diameter of perforation 34, when used in connection with a one (1) liter bailer having two ounces (2 oz.) of weights and having a downspout 30 that is 0.730 inches in diameter, results in a fill rate of about fifty seconds. It follows that the same opening in a half liter bailer of the same size and similarly weighted would produce a fill time of about twenty five seconds.

There are three primary factors that influence how fast bailer 10 will fill: 1) the diameter of downspout 30; 2) the combined mass of weights 18 and 28, and the diameter of perforation 34. Based upon the perforation and downspout sizes and weights disclosed herein, the optimal size of perforations for bailers having differing weights and downspouts of differing sizes may be empirically determined.

Another problem in the bailer industry is caused by the rapid emptying of bailers after a sample has been collected. A too-rapid emptying can also create agitation in the sample, thereby skewing laboratory test results. It has been observed that the provision of perforation 34 slows the emptying flow rate by about twenty five per cent (25%), thereby further alleviating the agitation problem.

Another advantage of the novel structure is its reduction of a need for a VOC device (not depicted). Such devices are used in the industry to momentarily unseat a valve such as check ball 22 from check ball seat 24 when the sample is being deposited into a plurality of vials. For example, where the collected sample is to be distributed into ten (10) vials, a VOC is used to momentarily lift check ball 22 from seat 24 to enable about one tenth ($1/10^{th}$) of the sample to flow from the bailer into a first vial. The process is then repeated until all vials have been filled.

Provision of perforation 34 reduces the need for a VOC, especially in those cases where the bailer is less than half filled. In such a case, the bailer user merely covers perforation 34 with a thumb until downspout 30 is in proper alignment with the mouth of a vial. This creates a vacuum in the space below the perforation and above the liquid level. The thumb is then lifted and the desired amount of sample is allowed to flow into the vial. Perforation 34 is then covered again and the process is repeated. This not only eliminates the need for a VOC when the bailer is about half full or less, it also prevents contamination of the sample as often happens when a VCO is used and the sample contacts the user's hand as it flows out of the bailer into the vial.

When the bailer is more than half full, closing perforation 34 with a thumb will slow the flow rate of the liquid from the bailer but may not stop it. In such cases, a VOC may still be used.

FIG. 2 and FIG. 2A are like FIGS. 1 and 1A with the exception that boss 36 is eliminated and perforation 34 is formed in plug 32 only. The use of boss 36 is preferred because it helps the user locate perforation 34.

Figure 3:
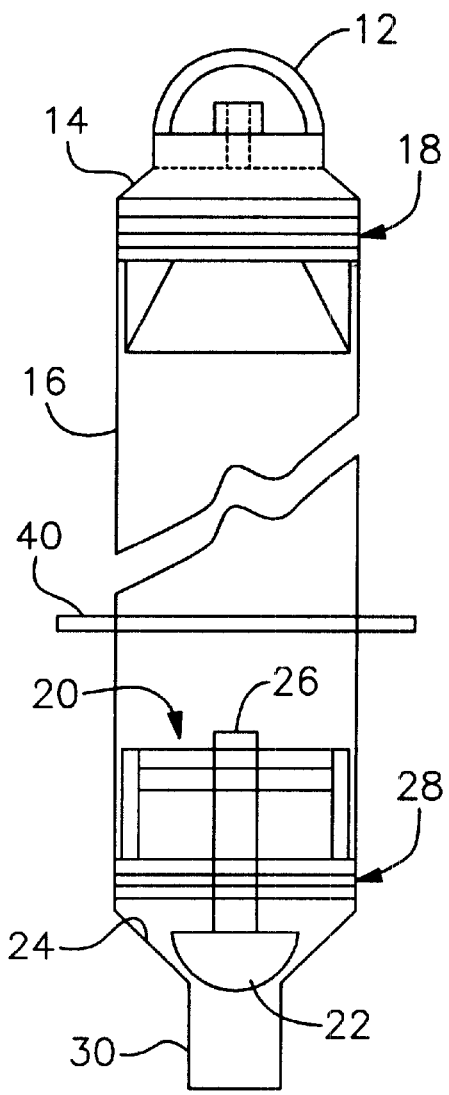
FIG. 3 is a side elevational view of a third embodiment.
Figure 3A:
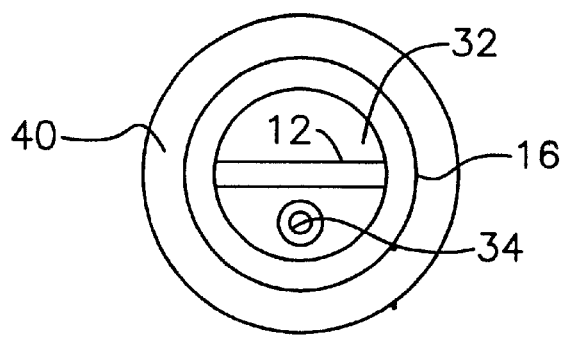
FIG. 3A is top plan view of said third embodiment.
Figure 3B:
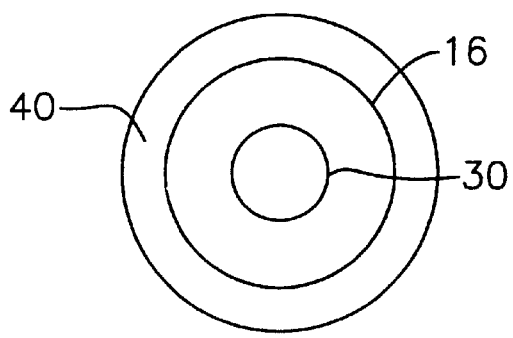
FIG. 3B is a bottom plan view of said third embodiment.
Figure 4:
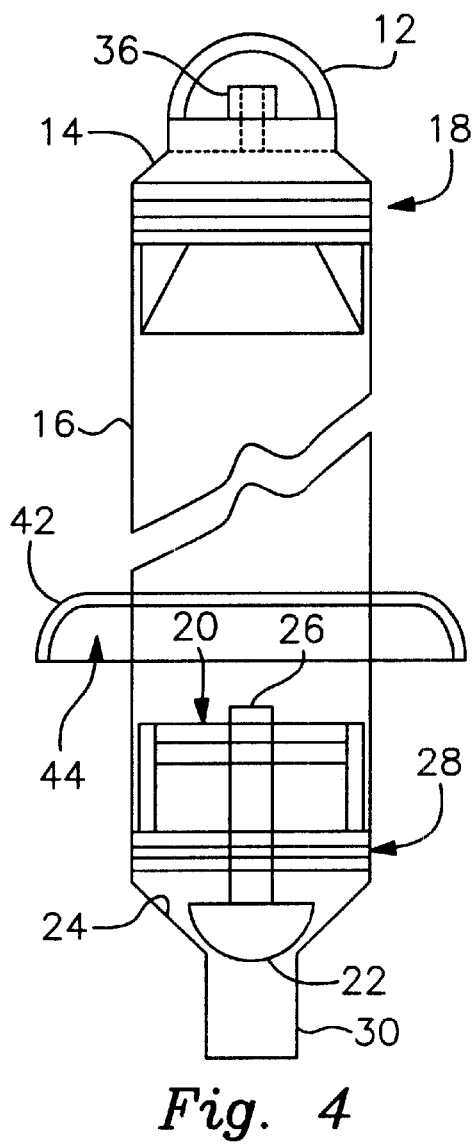
FIG. 4 is a side elevational view of a fourth embodiment.
Figure 4A:
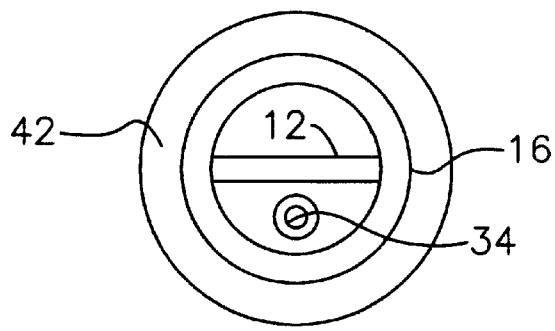
FIG. 4A is a top plan view of said fourth embodiment.
Figure 4B:
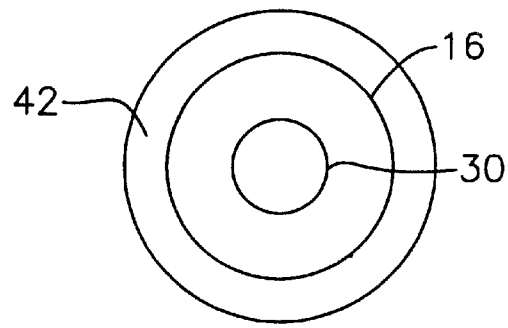
FIG. 4B is a bottom plan view of said fourth embodiment.

FIGS. 3, 3A, and 3B depict a third embodiment. At least one baffle wall 40 is secured to tubular main body 16 by suitable means to provide a braking means that prevents rapid sinking and thus rapid filling of the bailer. Baffle wall 40 could have a flat profile as depicted in FIG. 3, where it extends radially outwardly from the external wall of tubular main body 16 in normal relation thereto, or it could have a parachute profile 42, including a downward facing concavity 44, as depicted in FIGS. 4, 4A, and 4B, for example. The rate of descent is affected by the amount of weights 18, 28, as in the earlier embodiments, as well as the diameter and number of rings and their shape. Empirical testing would be required to determine optimal ring diameters and shapes to achieve various desired rates of descent. In both the third and fourth embodiments, the baffle wall or walls may be used with or without plug 32 and perforation 34.

Figure 5:
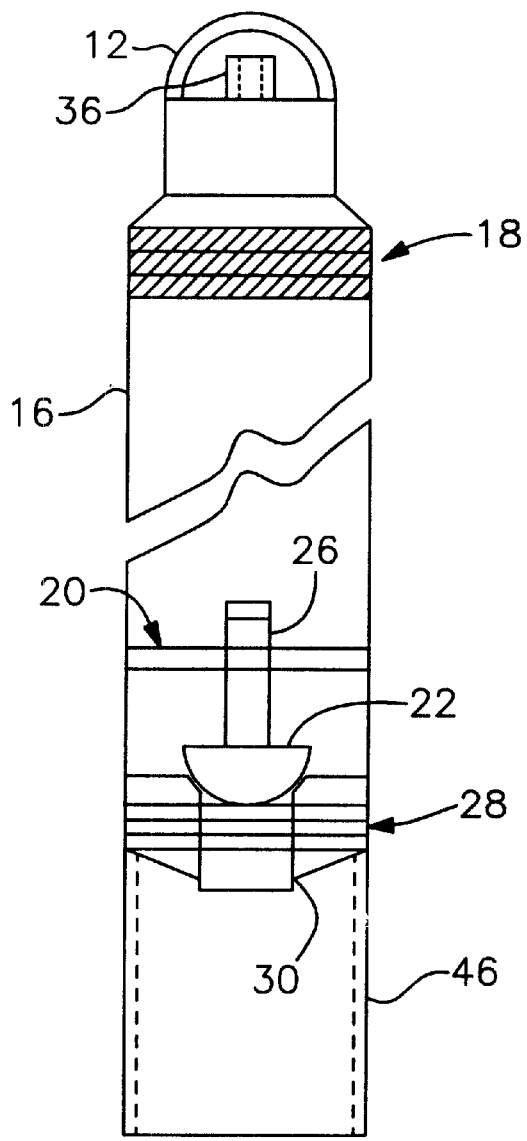
FIG. 5 is a side elevational view of a fifth embodiment.
Figure 5A:
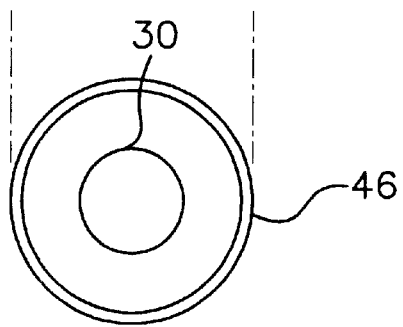
FIG. 5A is a bottom plan view of said fifth embodiment.

FIGS. 5 and 5A depict a fifth embodiment where a tubular stabilizer 46 is secured by suitable means to a lower end of bailer main body 16, in leading relation thereto. Stabilizer 44 must fill with liquid before check ball 22 is unseated. This structure inhibits tilting of the bailer as it slowly descends into the liquid being sampled, i.e., it helps maintain the bailer in an upright configuration as it descends into the liquid being sampled. As in the third and fourth embodiments, stabilizer 46 may be used with or without the plug and perforation of the first two embodiments.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A bailer, comprising:

an elongate, tubular main body having a hollow interior;

said elongate, tubular main body having an open upper end and a lower end;

a plug for closing said open upper end;

a perforation of predetermined size formed in said plug;

a check ball and a check ball seat disposed at said lower end of said bailer, said check ball lifting from said check ball seat, when said bailer is lowered into a body of liquid fluid, in response to an inflow of liquid fluid into said hollow interior;

said open lower end having a diameter substantially larger than a diameter of said perforation;

whereby air in said hollow interior is constrained to flow out of said hollow interior through said perforation as said liquid fluid flows into said hollow interior;

whereby a back pressure is created by said air because said air cannot flow through said perforation at a rate of flow that exceeds the rate of flow of said liquid fluid into said hollow interior;

whereby liquid fluid flows slowly into said hollow interior;

whereby said bailer descends into said liquid body at a slow rate of speed; and whereby agitation of said liquid fluid is reduced.

2. The bailer of claim 1, further comprising:

a boss means formed on said plug;

a throughbore formed in said boss means; and said throughbore being in open fluid communication with said perforation.

3. The bailer of claim 1, further comprising;

a first weight means secured to said elongate, tubular main body near a lowermost end thereof.

4. The bailer of claim 3, further comprising:

a second weight means secured to said elongate, tubular main body near an uppermost end thereof.

5. The bailer of claim of claim 3, wherein said perforation has a diameter between about 0.030 to 0.10 inches.

6. The bailer of claim 1, further comprising a tubular stabilizer secured to said lower end of said elongate main body, said tubular stabilizer extending in leading relation to said lower end.

7. A bailer, comprising:

elongate, tubular main body having a hollow interior;

said elongate, tubular main body having an open upper end and a lower end;

a check ball and a check ball seat disposed at a lower end of said bailer, said check ball lifting from said check ball seat, when said bailer is lowered into a body of liquid fluid, in response to an inflow of liquid fluid into said hollow interior;

at least one annular baffle wall mounted to an external wall of said elongate, tubular main boby at a preselected location thereon;

whereby said bailer descends into said liquid body at a slow rate of speed;

whereby liquid fluid flows slowly into said hollow interior;

whereby agitation of said liquid fluid is reduced.

8. The bailer of claim 7, wherein said at least one annular baffle wall is flat, extending radially outwardly from said external wall in normal relation thereto.

9. The bailer of claim 8, wherein said annular baffle wall includes a downwardly opening concavity.

10. The bailer of claim 7, further comprising a tubular stabilizer secured to said lower end of said elongate main body, said tubular stabilizer extending in leading relation to said lower end.

11. The bailer of claim 7, further comprising:

a plug for closing said open upper end; and a perforation of predetermined size formed in said plug;

whereby air in said hollow interior is constrained to flow out of said hollow interior through said perforation as said liquid fluid flows into said hollow interior;

whereby a back pressure is created by said air because said air cannot flow through said perforation at a rate of flow that exceeds the rate of flow of said liquid fluid into said hollow interior.

12. The bailer of claim 11, wherein said at least one annular baffle wall is flat, extending radially outwardly from said external wall in normal relation thereto.

13. The bailer of claim 12, wherein said annular baffle wall includes a downwardly opening concavity.

14. The bailer of claim 11, further comprising:

a boss means formed on said plug;

a throughbore formed in said boss means; and said throughbore being in open fluid communication with said perforation.

* * * * *